(12) United States Patent
Potashkin

(10) Patent No.: US 8,772,468 B2
(45) Date of Patent: Jul. 8, 2014

(54) SPLICE VARIANT SPECIFIC MESSENGER RNA TRANSCRIPTS AS BIOMARKERS OF PARKINSON'S DISEASE

(75) Inventor: Judith A. Potashkin, Gurnee, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 207 days.

(21) Appl. No.: 13/240,821

(22) Filed: Sep. 22, 2011

(65) Prior Publication Data
US 2013/0079235 A1   Mar. 28, 2013

(51) Int. Cl.
*C07H 21/04* (2006.01)

(52) U.S. Cl.
USPC ...................................................... 536/24.33

(58) Field of Classification Search
None
See application file for complete search history.

*Primary Examiner* — Michele K Joike
(74) *Attorney, Agent, or Firm* — Joseph A. Fuchs; Ungaretti & Harris LLP

(57) ABSTRACT

The present invention provides a method and a diagnostic kit for diagnosing the presence of Parkinson's disease in a human subject. The method includes the steps of: (1) extracting RNA molecules from a blood sample of the human subject to define a test sample; (2) measuring the amount of each RNA molecule having Sequence ID Nos. 1-14 in the test sample; (3) comparing the amount of each of the RNA molecules having Sequence ID Nos. 1-14 to the amount of RNA molecules having Sequence ID Nos. 1-14 present in a control sample to determine how many of the RNA molecules of Sequence ID Nos. 1-14 are present in a significant amount in the test sample greater or less than in the control sample to define a number of biomarkers; and (4) diagnosing the presence of Parkinson's disease in the human subject if the number of biomarkers is equal to or greater than five.

2 Claims, 8 Drawing Sheets
(1 of 8 Drawing Sheet(s) Filed in Color)

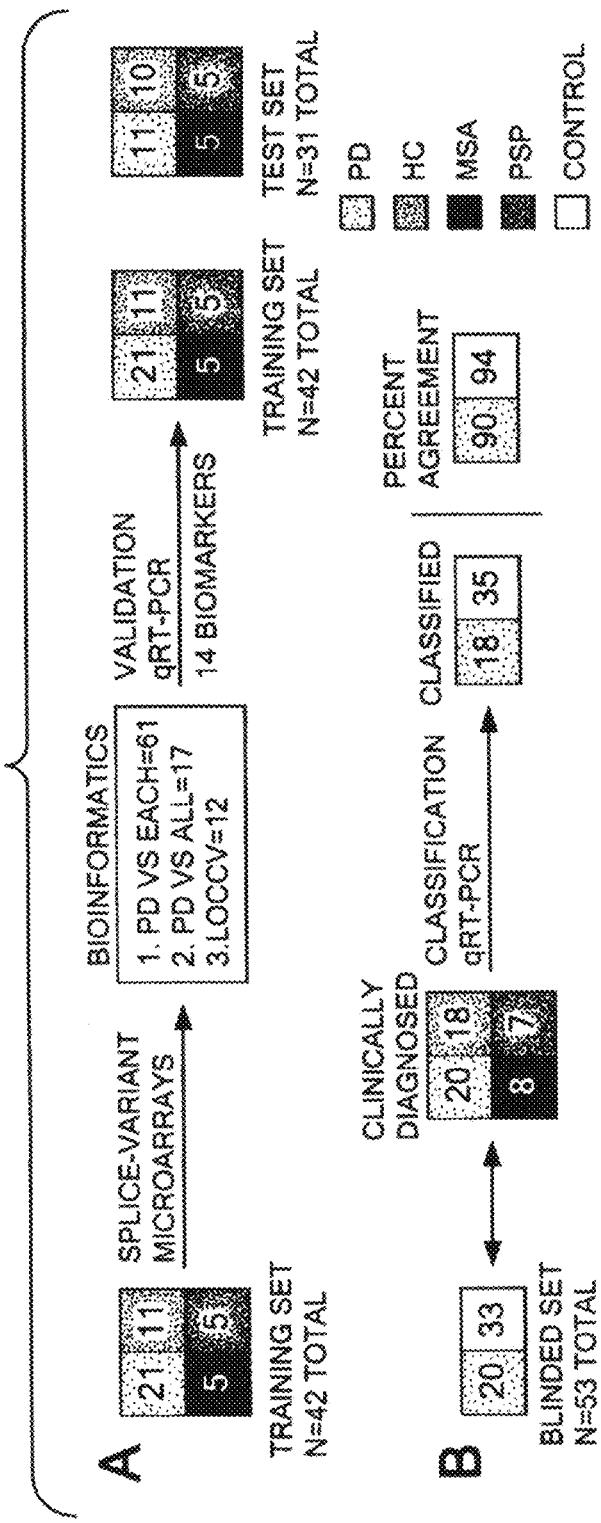
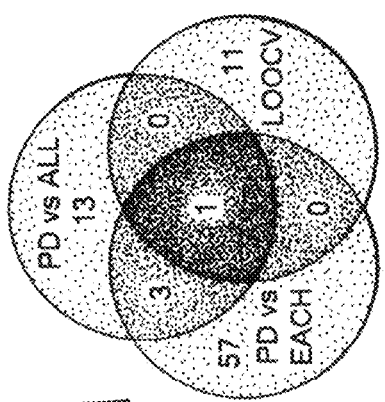
FIG. 1
FIG. 2A

FIG. 6A

| EVENT No.² | NAME | EVENT LOCATION¹ | IDENTIFIER² | 5' (FORWARD) | 3' (REVERSE) | CYCLES |
|---|---|---|---|---|---|---|
| 5315.014.2 | pmk2 ALTERNATIVE SPLICE DONOR | 4 | NM_182471.2 (SEQ ID NO: 1) | CACAGCCAGCCGGACTTCCT (SEQ ID NO: 15) | TTCAGATCCTGGATGTCCTTCTC (SEQ ID NO: 16) | 40 |
| 10826.005.1 | c5orf4 EXON SKIPPED | 4 <> 5 | NM_032385.3 (SEQ ID NO: 2) | GACATGGTGGATCCTGTGAAACT (SEQ ID NO: 17) | GAAAGATATCATGCACTGGTTGAAA (SEQ ID NO: 18) | 50 |
| 23499.058.1 | macf1 EXON SKIPPED | 39 <> 39 | NM_012090.4 (SEQ ID NO: 3) | ATGAGGCGCTCCAGGAAGA (SEQ ID NO: 19) | AGGTCACTGCTTCCTCCAGTTC (SEQ ID NO: 20) | 50 |
| 54886.003.1 | prg3 NOVEL EXON | 1 >< 2 | AX_050009.1 (SEQ ID NO: 4) | CGGGAGCCTGGACAGTTTT (SEQ ID NO: 21) | CCTACACAGCCATTTCTCACACCAT (SEQ ID NO: 22) | 40 |
| 11184.010.1 | map4k1 EXON SKIPPED | 2 <> 2 | NM_007181.3 (SEQ ID NO: 5) | GGACCTGGTGGTGGCACTGAAGA (SEQ ID NO: 23) | CGGCAAGTTTTCAATATGAGGAT (SEQ ID NO: 24) | 40 |
| 79971.007.1 | wls NOVEL EXON | 2 >< 3 | NM_001002292.3 (SEQ ID NO: 6) | CAAGCTAAACACCAACCAAATCAGAGAAA (SEQ ID NO: 25) | ATCACGGTAAGCCAGGAAA (SEQ ID NO: 26) | 40 |
| 6563.016.1 | slc14a1-s EXON SKIPPED | 8 <> 8 | NM_015865.6 (SEQ ID NO: 7) | CACTCATGTGCCTGCATGCT (SEQ ID NO: 27) | AACAGGCGCCGCTGCTATG (SEQ ID NO: 28) | 50 |
| 6563.016.1 | slc14a1-l EXON INCLUDED | 8 >< 8 | NM_015865.6 (SEQ ID NO: 8) | GCATAGCCAGCCGGGACTCAGT (SEQ ID NO: 29) | ACCCCAGAGTCCAAAGTAGATGTC (SEQ ID NO: 30) | 50 |
| 9343.019.2 | eftud2 EXON SKIPPED | 1 <> 1 | NM_004247.3 (SEQ ID NO: 9) | AGCAGGCCGAGAGATGGATGA (SEQ ID NO: 31) | CGGCTGTTGGGTAGTACTTCTTG (SEQ ID NO: 32) | 50 |
| 22818.003.2 | copz1 EXON SKIPPED | 1 <> 1 | NM_016057.1 (SEQ ID NO: 10) | GATTTTGTTGTGGGAAAGAGT (SEQ ID NO: 33) | TGACAGCTCCCCTAGATCTTTG (SEQ ID NO: 34) | 40 |

FIG. 6B

| | | | | | |
|---|---|---|---|---|---|
| 90338.007.1 | znf160 NOVEL EXON | 4 > < 5 | NM_198893.2 (SEQ ID NO: 11) | GGGTCCGTACGGACTTAAAATCT (SEQ ID NO: 35) | CGGATCCAGGAACGTTTCTG (SEQ ID NO: 36) | 40 |
| 4354.006.1 | mpp1 EXON SKIPPED | 2 <> 8 | NM_002436.3 (SEQ ID NO: 12) | GAGGCTGTATGCCATCCATTG (SEQ ID NO: 37) | GCAGGAGACCCGTTGGTGTA (SEQ ID NO: 38) | 40 |
| 7693.001.1 | znf134 EXON SKIPPED | 2 <> 2 | NM_003435.3 (SEQ ID NO: 13) | GGCCCCGGCGCAGAT (SEQ ID NO: 39) | GCAGCCAGAGTTCTCTCTGT (SEQ ID NO: 40) | 40 |
| 9821.005.1 | rb1cc1 EXON SKIPPED | 3 <> 3 | NM_014781.4 (SEQ ID NO: 14) | TCAGTTGCCAATCTCAAGCAA (SEQ ID NO: 41) | GCCACACGTCAGGCACTGT (SEQ ID NO: 42) | 50 |
| CONTROL | gapdh | | | CAACGGATTTGGTCGTATTGG (SEQ ID NO: 43) | TGATGGCAACAATATCCACTTTACC (SEQ ID NO: 44) | 40 |

| PCR PROTOCOL | POWER SYBR GREEN MIX (APPLIED BIOSYSTEMS, FOSTER CITY, CA) |
|---|---|
| 1. 95°C — 10 MIN | 25 ul rxns |
| 2. 95°C — 15 SEC | SYBR: 12.0 ul |
| 3. ANNEALING 56°C — 1 MIN | PRIMER: 2 ul |
| 4. EXTENSION 72°C — 30 SEC | WATER: 9 ul |
| 40-50 (STEP 2 TO 4) | cDNA: 2 ul |

[1] NUMBER REPRESENT EXONS
  > < REPRESENTS BETWEEN
  < > REPRESENTS SKIPPED
[2] EVENT AND IDENTIFIER NUMBERS LOCATED AT:
  http://www.ncbi.nlm.nih.gov/
  http://genome.ucsc.edu/cgi-bin/hgGateway

SPLICE VARIANT SPECIFIC MESSENGER RNA TRANSCRIPTS AS BIOMARKERS OF PARKINSON'S DISEASE

FEDERALLY SPONSORED RESEARCH OR DEVELOPMENT

This invention was made with government support under United States Army Medical Research and Materiel Command NETRP grant number W81XWH-09-0708. The government has certain rights in the invention

TECHNICAL FIELD

The present invention generally relates to a method of diagnosing Parkinson's disease in a human subject based on the presence of at least five splice variant RNA molecules from a set of fourteen candidate splice variants in a blood sample taken from the human subject.

REFERENCE TO SEQUENCE LISTING

The instant application contains a Sequence Listing which has been submitted in ASCII format via EFS-Web and is hereby incorporated by reference in its entirety. Said ASCII copy, created on Sep. 22, 2011, is named 112461US.txt and is 10,397 bytes in size.

BACKGROUND OF THE INVENTION

Parkinson's disease ("PD") is the second most prevalent chronic neurodegenerative disease, affecting 1-3% of individuals 65 years and older. Diagnosis of PD is based on classical motor symptoms including resting tremor, rigidity, bradykinesia and postural instability. By the time PD is clinically diagnosed 60-80% of the neurons in the substantia niagra pars compacta have died leading to irreversible brain damage. Approximately 5% of the incidences of PD are familial, whereas the majority of the cases are idiopathic most likely caused by exposure to environmental factors and genetic susceptibility. Some environmental causes of PD are known; they include pesticides, fungicides, heavy metals, MPTP and traumatic brain injury. Thus, early detection of PD would be beneficial so that counseling with regards to avoidance of neurotoxins could be initiated and therapeutic intervention may be offered to patients. In addition agents that are promising as being neuroprotective for PD, including but not limited to creatine, rasagiline and minocycline, which are currently in Phase III trials, may in the future be prescribed for high risk individuals. Therefore, the identification of accurate and sensitive minimally invasive molecular biomarkers that could be used to identify PD patients would be valuable.

The loss of nigrostriatal dopamine ("DA") neurons in PD is reflected in changes in gene expression within postmortem brains. Genes related to dopamine neurotransmission, synaptic function, electron transport, ubiquitin-proteasomal system, cytoskeletal maintenance, cell cycle and adhesion are dysregulated in PD patients (1-3). Brain tissue, however, is not a useful source for PD biomarkers. In contrast, blood biomarkers would be very useful since they can be easily obtained. In this regard, it is clear that the immune system responds to changes in DA (4). This is not unexpected since catecholamines are synthesized from tyrosine in lymphocytes and macrophages (5). In addition, dopamine receptors are expressed in low abundance in T lymphocytes and monocytes, moderately expressed in neutrophils and eosinophils, and abundantly expressed in B cells and natural killer cells (6) and DA transporters are expressed in lymphocytes (7). DA receptors are elevated and DA is reduced in the blood of PD patients compared to age-matched controls (8, 9). DA also affects the activity of regulatory T cells (10). Recently a "brain-to-T cell" pathway was proposed to explain how peripheral T lymphocytes might respond to DA in the brain based on the fact that T lymphoblast can cross the blood-brain barrier (11). It is not clear whether the changes in gene expression in the blood play a role in the etiology or progression of PD, but one intriguing study showed that CD4+ lymphocytes infiltrated the postmortem brains of PD patients (12). In addition, using a mouse model of PD the study showed that CD4+ T cells caused cell-mediated dopaminergic toxicity that lead to neurodegeneration (12). Thus, identification of changes in gene expression in the blood may provide beneficial information with regard to the cause or progression of PD.

More recently, RNA biomarkers that are predictive of PD were identified in blood cells (13, 14). In one study, 22 genes that were identified that were differentially expressed in PD patients compared to controls (14). In another study, the expression of the genes SCNA, which encodes a synuclein, and the heme metabolism genes ALAS2, FECH and BLVRB were coordinately up-regulated in blood cells of PD patients compared to controls (14). In addition the expression of SCNA was induced in the substantia nigra of PD patients (14). In the original RNA biomarker study standard cDNA microarrays were used and therefore changes in the abundance of mRNAs were monitored, which is a reflection of transcription and RNA stability.

Few studies have searched for changes in pre-mRNA splicing that occur in PD. In one study differential expression of a parkin splice variant in leukocytes of PD patients was observed (15). More recently, splicing was found to be dysregulated in PD patients (16). Because having additional RNA biomarkers would be very helpful, and since most pre-mRNAs are alternatively spliced, we chose to search for splice variant specific mRNA biomarkers of PD. Most splice variant specific markers would be masked in a standard cDNA microarray study since the up-regulation of one splice variant and the down-regulation of another variant of the same pre-mRNA might cancel each other out such that the overall abundance is unchanged. Because of this, many potential splice variant-specific RNA biomarkers may have been overlooked in earlier studies. In this study, we used splice variant-specific microarrays to identify 14 mRNA biomarkers of PD.

BRIEF SUMMARY OF THE INVENTION

The present invention provides a method and a diagnostic kit for diagnosing the presence of Parkinson's disease in a human subject. The method includes the steps of: (1) extracting RNA molecules from a blood sample of the human subject to define a test sample; (2) measuring the relative amount of each RNA molecule having Sequence ID Nos. 1-14 in the test sample; (3) comparing the relative amount of each of the RNA molecules having Sequence ID Nos. 1-14 to a relative amount of RNA molecules having Sequence ID Nos. 1-14 present in control samples to determine how many of the RNA molecules of Sequence ID Nos. 1-14 are present in a significantly different amount to define a number of biomarkers; and (4) diagnosing the presence of Parkinson's disease in the human subject if the number of biomarkers is equal to or greater than five.

The present invention further provides a method and a kit for differentiating a PD patient from a patient afflicted with MSA or PSP. The method includes the steps of: (1) extracting RNA molecules from a blood sample of the human subject to define a test sample; (2) measuring the relative amount of splice variant copz1 RNA having Sequence ID No. 10 in the test sample; (3) comparing the relative amount of copz1 having Sequence ID No. 10 in a PD, MSA and PSP control samples and (4) diagnosing the presence of Parkinson's disease in the human subject if the amount of copz1 in the test sample and the control samples are significantly different.

BRIEF DESCRIPTION OF THE DRAWINGS

The patent or application file contains at least one drawing executed in color. Copies of this patent or patent application publication with color drawing will be provided by the Office upon request and payment of the necessary fee.

FIGS. 1A and 1B are schematics of a workflow used to identify splice variant specific biomarkers of PD. The numbers inside the boxes correspond to the number of samples.

FIG. 2A is a Venn diagram identifying splice events which were differentially expressed in PD patients compared to controls and identified by microarray data analysis in which PD patients were compared to each control group (HC, MSA or PSP) individually, a single control group that included HC, MSA and PSP participants or using the leave-one-out cross-validation method.

FIG. 4A shows ΔCt graphs of pkm2, slc14a1-s, slc14a1-l and macf1 from healthy controls compared to PD, MSA and PSP patients. FIG. 4B shows ΔCt graphs of copz1 from MSA and PSP patients compared to PD patients and healthy controls. FIG. 4C shows ΔCt graphs of wls and znf160 from PSP patients compared to PD, healthy control and MSA patients. A student t test was used to compare groups. *p<0.05, p<0.005 and *p<0.001. Mean ΔCt values are displayed with error bars indicating SEM. Gapdh mRNA was used as a control. HC is healthy control, PD is Parkinson's disease, MSA is multiple system atrophy and PSP is progressive supranuclear palsy patients.

FIG. 6 is a table providing identifying information for the mRNA sequences that result from an alternative splicing event (i.e., splice variants) that are used to diagnose the presence of Parkinson's disease in a human patient and the specific forward and reverse primers for amplifying the splice variants from blood samples obtained from the human subjects.

DETAILED DESCRIPTION OF THE INVENTION

Figure 2B:
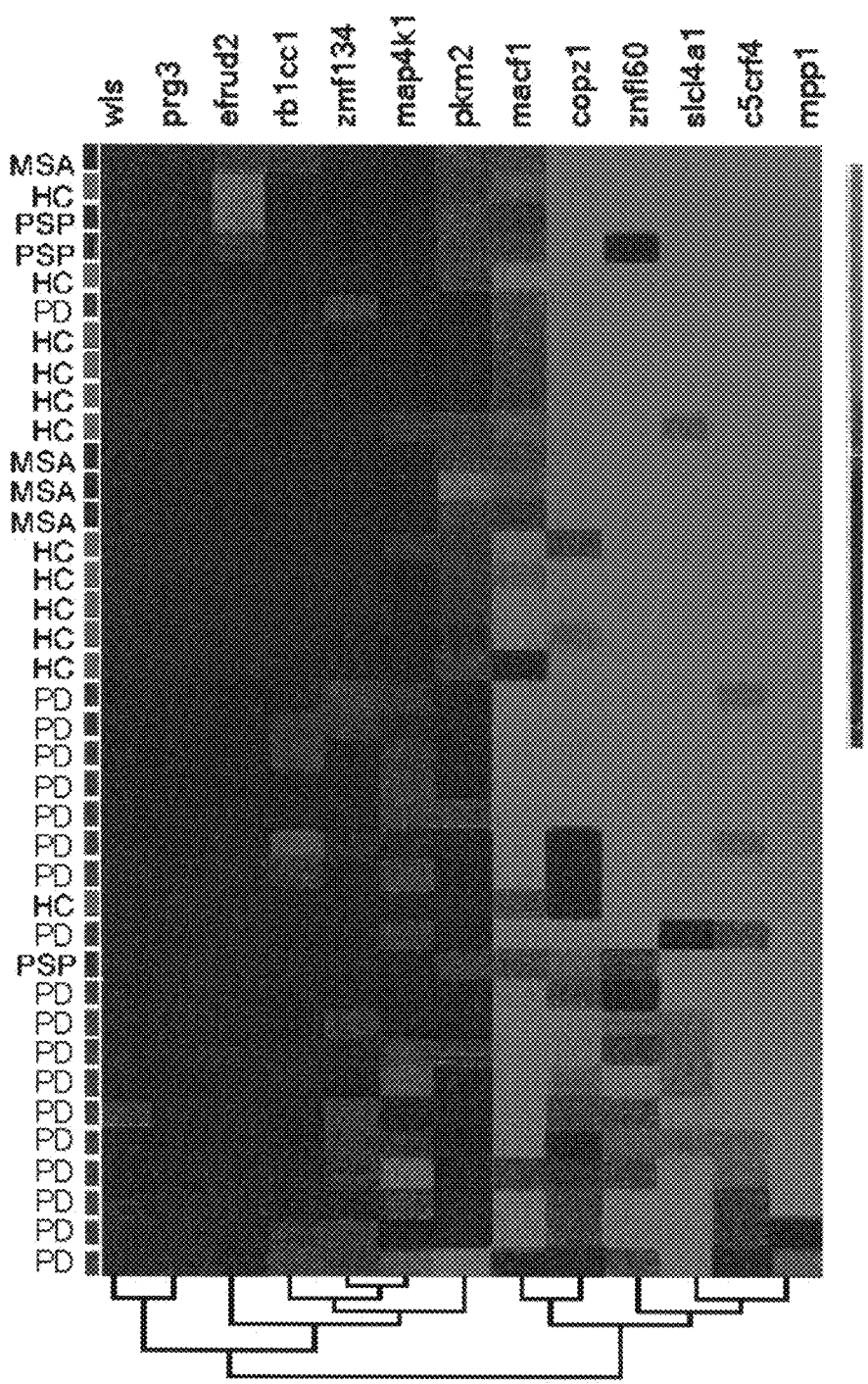
FIG. 2B is a heat map of unsupervised hierarchical clustering analysis of abundance of splice events in PD and controls. The analysis indicated that PD patients can be clustered together using the 14 validated biomarkers. Depicted are the microarray-profiled top splice events, with the most significant changes in relative abundance between PD patients and controls hierarchically clustered. Each column in the heatmap corresponds to a PD patient or a control. Each row represents the relative level of abundance of a single splice variant. The splice variants are arranged from top to bottom in the order from the least abundant splice variant to the most abundant variant. Each splice variant is denoted by the name of the mRNA. Color scales representing splice variant expression with red representing high abundance relative to the mean abundance; blue representing low abundance relative to the mean abundance; and gray representing no significant change in abundance level between the sample and control.

While this invention is susceptible to embodiments in many different forms, it is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

The present invention provides a method of detecting Parkinson's disease in a human subject based on an analysis of a whole blood sample of the human subject. RNA is extracted from the blood sample and amplified through a process such as, for example, real time PCR. Fourteen RNA molecules (Sequence ID Nos. 1-14) identified in FIG. 6 have been found useful in diagnosing the presence of Parkinson's disease in blinded samples. If five or more of these RNAs are found in significant quantities greater or less than are contained in a control sample, a positive diagnosis of the presence of Parkinson's disease in the human subject is made. Early detection of PD could improve disease management and enable potential future neuroprotective therapies to be introduced at a stage when they would provide the greatest benefit. In addition, the biomarkers may be useful in identifying unknown environmental factors that play a role in the development of PD. The present invention also provides forward and reverse primers (Sequence ID Nos. 15-42) that can be used in a PCR process to detect the presence of the biomarker RNA molecules of Sequence ID Nos. 1-14. The present invention further provides a kit containing the primers Sequence ID Nos. 15-42 for use in a PCR Parkinson's disease diagnostic.

Method of Diagnosing PD in a Human Subject

The method for diagnosing the presence of Parkinson's disease in a human subject includes the steps of: (1) extracting RNA molecules from a blood sample of the human subject to define a test sample; (2) measuring the relative amount of each RNA molecule having Sequence ID Nos. 1-14 in the test sample; (3) comparing the relative amount of each of the RNA molecules having Sequence ID Nos. 1-14 to a relative amount of RNA molecules having Sequence ID Nos. 1-14 present in a control sample to determine how many of the RNA molecules of Sequence ID Nos. 1-14 are present in a significantly different amount to define a number of biomarkers; and (4) diagnosing the presence of Parkinson's disease in the human subject if the number of biomarkers is equal to or greater than five.

One preferred method of measuring the amount of RNA molecules is by PCR and more preferably real time PCR. In a preferred form of the invention, the PCR will be carried out using the primers having Sequence ID Nos. 15-42.

The blood sample, in a preferred form of the invention, is whole blood. The method of extracting RNA from whole blood is preferably accomplished using a PAXgene blood RNA kit in accordance with the instructions provided in the kit. After the extracting step, the extract is subjected to DNase I digestion as is well known in the art.

In comparing the relative quantities or amounts of each of the RNA molecules having Sequence ID Nos. 1-14 to the relative quantities of these RNAs in a control sample, the biomarker must be either significantly more or less abundant than a control sample. What is meant by "significant" or "significantly" is that one would have to subject the sample having the lower amount to at least one half of one PCR cycle more in order to equal the higher amount. There must be at least five biomarkers present in the test sample that meet these criteria to reach a positive diagnosis of Parkinson's disease.

In a preferred form of the invention, splice variants identified in FIG. 6 are targeted for amplification, namely pkm2, c5orf4, macf1, prg3, map4k1, wls, slc 14a1-s, slc 14a1-1, eftud2, copz1, znf160, mpp 1, znf134, and rb1cc1 which are candidate biomarkers.

It is also contemplated that the primers having Sequence ID Nos. 15-42 could be included in a Parkinson's disease diagnostic kit with a set of instructions on how to use the kit in a PCR procedure to diagnose the presence of Parkinson's disease in a human subject. The kit would also include the necessary polymerases, deoxynucleoside tri-phosphates ("dNTPs"), magnesium chloride and reaction buffer.

EXAMPLES

Materials and Methods

Clinical Study.

Early stage PD patients (1-2.5 on the Unified Parkinson Disease Rating Scale ("UPDRS") and age-matched healthy and neurodegenerative disease controls were enrolled in the PROBE study (Prognostic Biomarker Study, clinical trial #NCT00653783) from the Parkinson Study Group at the University of Rochester (17). Clinical diagnosis of PD was based on the United Kingdom Parkinson's disease Society Brain Bank criteria requiring the presence of two cardinal features (bradykinesia, rigidity, rest tremor or postural instability), none of the exclusion criteria and at least three supportive features (18). The healthy controls had no history of neurological disease and a Mini-Mental State Examination ("MMSE") test score that was ≥27. The healthy controls were recruited from spouses and non-blood relatives. Disease controls included multiple system atrophy ("MSA") and progressive supranuclear palsy ("PSP"). A diagnosis of probable MSA was based on Consensus Criteria (19) and probable PSP based on NINDS-PSP Criteria (20). Exclusion criteria for all groups included use of anticoagulants, diagnosis of a bleeding or blood disorder, a history of anemia with a documented hematocrit <30 and known pregnancy. The Institutional Review Board of University of Rochester School of Medicine approved the study protocol.

RNA Isolation and Quality Control.

Whole blood was collected in PAXgene tubes (Qiagen, Valencia, Calif.) to ensure stabilization of intracellular RNA. Tubes containing blood were immediately incubated at room temperature for 24 h. RNA was extracted using the PAXgene blood RNA kit according to the manufacturer's protocol followed by DNase I digestion. RNA quality was determined by spectrophotometry and using the RNA 6000 NanoChip kit and an Agilent 2100 Bioanalyzer (Agilent Technologies, Santa Clara, Calif.). Samples with RNA integrity values >7.0 and absorbance 260/280 between 1.7 and 2.4 were used for further analysis.

Microarray Procedures.

Amplified and labeled cDNA was prepared using the NuGEN WT-Ovation™ Pico RNA Amplification System and the FL-Ovation™ cDNA Biotin Module V2 (NuGEN, CA). First strand cDNA was prepared by ExonHit Therapeutics, Inc (Gaithersburg, Md.) from total RNA using a first strand DNA/RNA chimeric primer mix (containing a DNA portion that hybridizes either to the 5' portion of the poly (A) sequence or randomly across the transcript) and reverse transcriptase. Fragmentation of the mRNA within the cDNA/mRNA complex created priming sites for DNA polymerase to synthesize a second strand, which included DNA complementary to the 5' unique sequence from the first strand chimeric primers. This method produces a double stranded cDNA with a DNA/RNA heteroduplex which was amplified using a SPIA™ DNA/RNA chimeric primer, DNA polymerase and RNase H in the SPIA™ process (NuGEN™, San Carlos, Calif.) (21). The RNA 6000 Nano kit was used to evaluate the quality of the amplified cDNA using the Agilent 2100 Bioanalyzer prior to hybridization. Standard methods were used to hybridize the samples to the SpliceArray™ (ExonHit Therapeutics, Inc, Gaithersburg, Md.) following recommendations of the manufacturer (Affymetrix, Santa Clara, Calif.). The arrays were stained and washed using the FS450-001 fluidics protocol prior to scanning with the GeneChip® Scanner 3000 7G (Affymetrix, Santa Clara, Calif.).

Microarray Data Analysis.

Data analysis was performed with Partek GS 6.5 software (St. Louis, Mo.). Three methods were used to identify splice variants that were differentially expressed in PD patients compared to controls.

Method 1. Identification of splice variants that are differentially expressed in PD patients compared to each control group. We performed analysis of variance (ANOVA) for pairwise comparisons between the group of PD samples versus each of the control groups (healthy controls ("HC"), multiple system atrophy ("MSA"), progressive supranuclear palsy ("PSP"). A cut-off of two-fold change and p-value of 0.05 was used to eliminated those splice events whose expression did not change significantly between the groups. FIG. 2A shows a Venn diagram analysis of the data was used to identify splice events which were differentially expressed selectively in only one pairwise comparison involving the PD group (PD vs HC, PD vs MSA and PD vs PSP). The union of the splice events identified by this comparison included 61 splice variants.

Method 2. Identification of splice variants that are differentially expressed in PD patients compared to all control groups. To assess the correlation between the expression of splice variants with binary diagnostic categories (PD vs. controls) were calculated using the Pearson correlation coefficient for all splice events.

Method 3. Identification of splice variants with optimized accuracy of prognostic prediction. In order to identify a group of splice events with optimized accuracy of prognostic prediction we applied a two-level nested leave-one-out cross-validation method ("LOOCV"). An "outer" ten-fold cross-validation was performed to estimate prediction error of the classifier on a test set, while a nested, "inner", nine-fold cross-validation was performed on the training data used to select the optimal classifier to be applied to the test set. We assessed K-Nearest Neighbor ("KNN") classification models with the number of neighbors from 1 to 12. Only events with a 2-fold expression change or greater were included in the analysis. The best performing (with the smallest prognostic prediction error) classification model contained 12 splice events.

Real Time PCR

The sequence of the splice variants that were identified by microarray analysis was retrieved from the UCSC genome browser and are shown in FIG. 6. Splice variant-specific primers were designed using Primer express software (Applied Biosystems, Foster City, Calif.) such that one of the primers spanned the splice junction (FIG. 6). The High Capacity RNA transcription kit (Applied Biosystems, Foster City, Calif.) was used to reverse transcribe 1 µg of total RNA according to the manufacturer's protocol. The sequence of the primers and the number of cycles used to amplify the products is presented in the table shown in FIG. 6. The DNA engine Opticon 2 Analyzer (Bio-Rad Life Sciences, Hercules, Calif.) was used for the real time PCR reactions. Each 25 µl reaction contained Power SYBR® dye and primers at a concentration of 0.05 mM. The amplification conditions used are as follows: denature at 95° C. for 15 sec, annealing at 56° C. for 1 min, extension at 72° C. for 30 sec for 40-50 cycles of amplification and a 7 min extension at 68° C. PCR products were run in 2% agarose gels and sequenced to verify specificity. Gapdh was used as an internal control. Samples were loaded in triplicates. No cDNA template negative controls and PD, MSA and PSP controls were run in every experiment. Amplification efficiencies were higher than 90% for each primer set. Expression data as analyzed using the comparative delta Ct method.

Statistical Analysis.

Comparisons between groups was done using a student t test.

Results

The overall design of this study is presented in FIGS. 1A and 1B. RNA was obtained from study participants including PD patients, healthy controls and disease controls, which included patients clinically diagnosed with MSA and PSP. Table 1 presents the data on the study participants. The only difference between the participants used in the coded and blinded samples is that there was a higher male:female ratio in the blinded samples (9:1) compared to the coded samples (3:1).

TABLE 1

Information about study participants.

| | PD | | HC | | MSA | | PSP | |
| --- | --- | --- | --- | --- | --- | --- | --- | --- |
| | C | B | C | B | C | B | C | B |
| number | 31 | 20 | 21 | 18 | 10 | 8 | 10 | 7 |
| median age | 61 | 58 | 58 | 57 | 64 | 63 | 76 | 67 |
| average age | 63 | 61 | 61 | 61 | 63 | 64 | 73 | 68 |
| % female | 25 | 10 | 50 | 77 | 50 | 37 | 44 | 43 |
| % male | 75 | 90 | 50 | 33 | 50 | 63 | 56 | 57 |
| Hoehn & Yahr | 2 | 2 | | | | | | |

C is coded samples,
B is blinded samples,
HC is healthy control,
PD is Parkinson's disease,
MSA is multiple system atrophy and
PSP is progressive supranuclear palsy patients.

RNA from the training set was used to screen splice variant-specific microarrays in order to identify mRNAs whose expression was at least 2-fold up- or down-regulated in PD patients compared to healthy and disease controls. The data from the microarray screen was analyzed by three different methods to optimize the number of potentially useful splice variants identified. In the first method, differentially expressed splice variants in PD patients was compared to each control group individually (PD vs each). The results identified 61 splice variants whose expression was differentially expressed in PD patients compared to healthy, MSA and PSP controls (FIG. 2A). Ten splice variants identified by this analysis were validated using the training and test set of samples in qPCR assays including c5orf4, wls, macf1, prg3, eftud2, pkm2, rb1cc1, slc14a1-s, slc14a1-1 and mpp1.

Differentially expressed splice variants in PD patients were also compared to all controls without distinguishing between the types of control (PD vs all). This analysis produced 17 splice variants that were differentially expressed between PD and controls (FIG. 2A). Seven of these markers were validated in qPCR assays including c5orf4, wls, slc14a1-s, slc14a1-1, copz1, znf160 and mpp1.

In a third analysis, LOOCV was used to optimize the accuracy of prognostic prediction of the splice variants for identifying PD patients (FIG. 2A). From this set of candidate biomarkers, three were validated in qPCR assays including c5orf4, map4k1 and znf134. Only c5orf4 was identified by all three methods of analysis.

Figure 4:
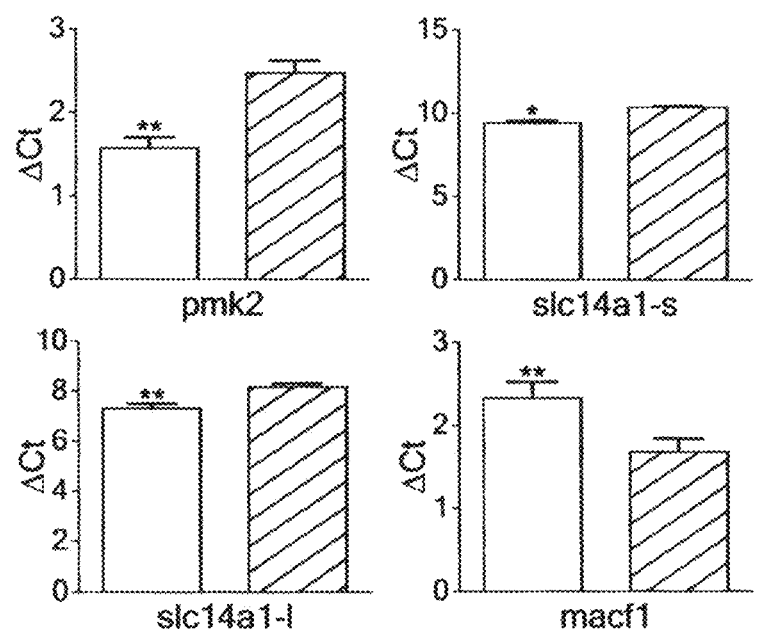
FIGS. 4A-C are representative ΔCt graphs of biomarkers from a test set of study participants.
Figure 4:
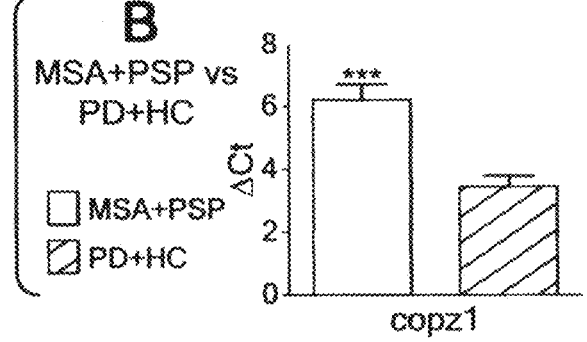
Figure 4:
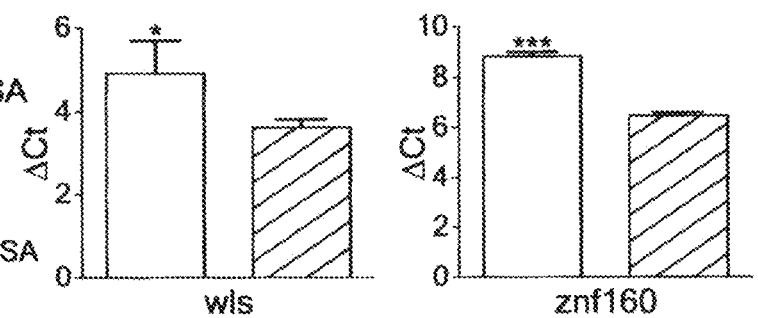

The healthy controls were also compared to PD, MSA and PSP patients, disease controls compared to PD patients and healthy controls combined and PSP patients compared to PD, HC and MSA participants combined in order to determine if particular biomarkers would be helpful in identifying healthy and disease controls (FIG. 4). The results showed that pkm2, slc14a1-s, slc14a1-1 and macf1 splice variants are expressed differently in healthy individuals compared to the PD patients and the neurological controls. In addition, copz1 is less abundant in MSA and PSP then in HC and PD combined since more PCR cycles were required to amplify the mRNA. Finally, wls and znf160 are downregulated in PSP patients compared to PD, HC and MSA participants as a group.

Figure 2C:
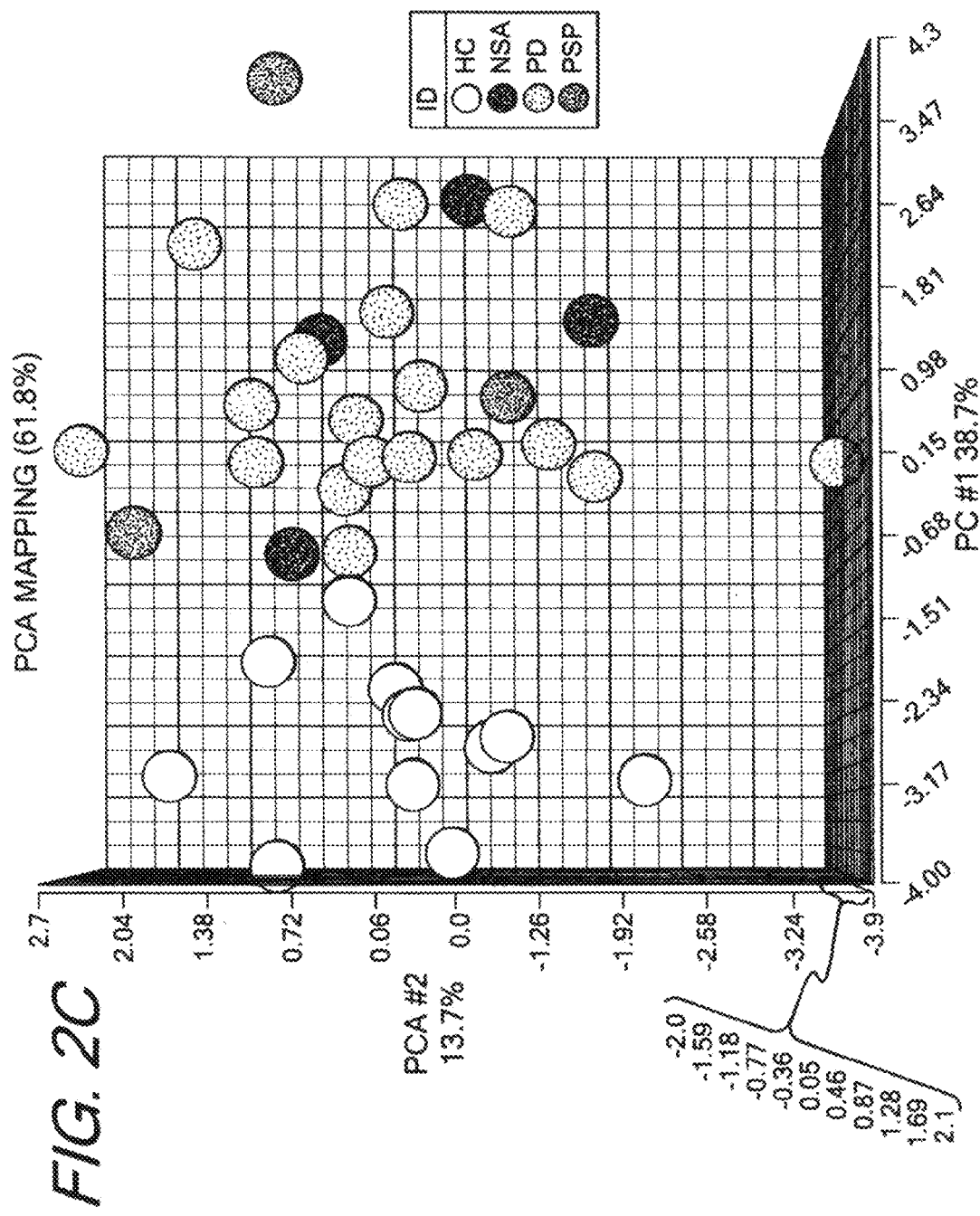
FIG. 2C shows PCA analysis of the validated biomarkers, which indicates that they should be useful in classifying PD patients separately from controls. HC is healthy control, PD is Parkinson's disease patient, MSA is multiple system atrophy patient and PSP is progressive supranuclear palsy patient.
Figure 3:
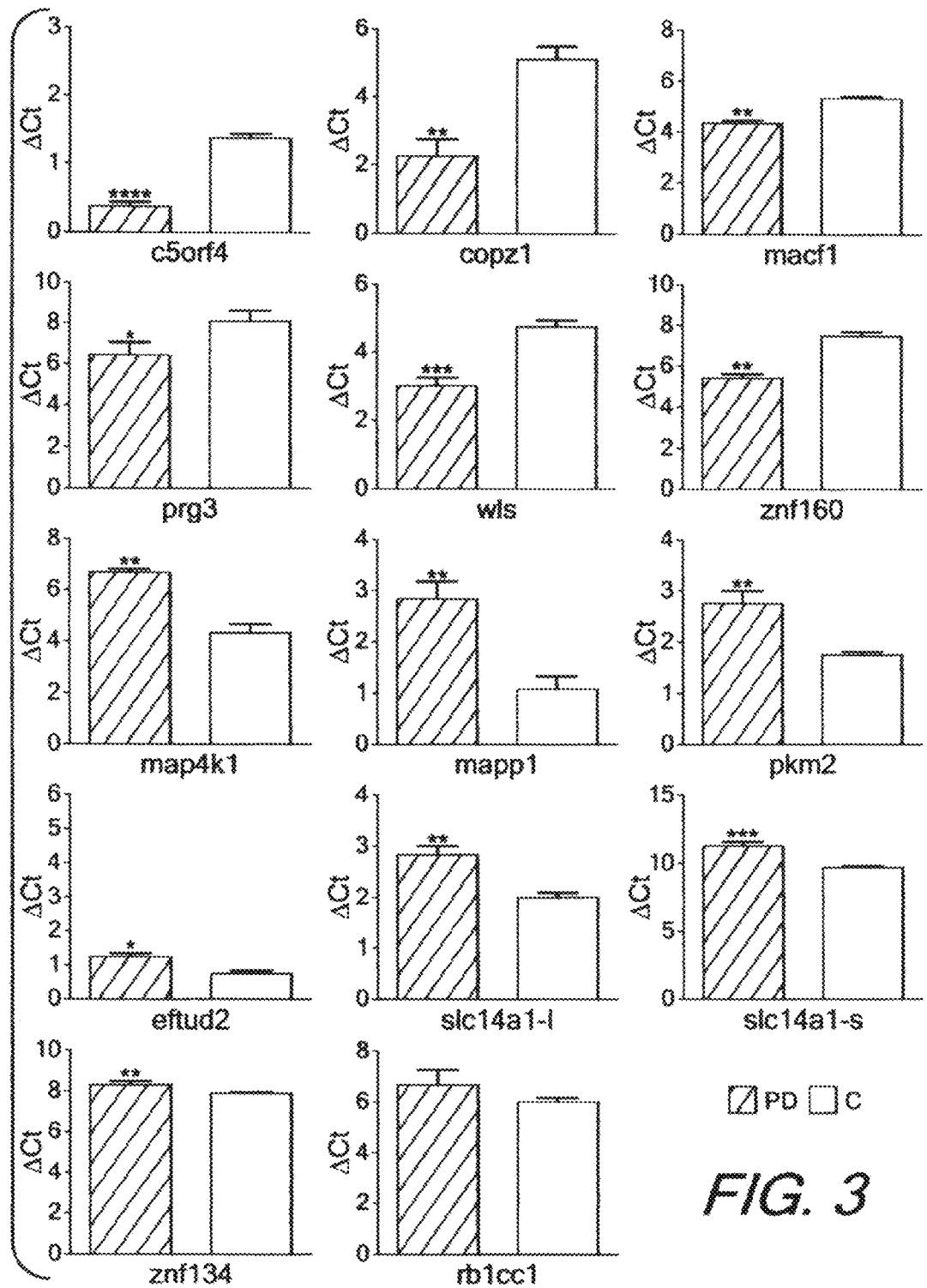
FIG. 3 are representative ΔCt graphs of biomarkers from the test set of study participants comparing PD patients with controls. A student t test was used to compare groups. *p<0.05, p<0.005 and *p<0.001. Mean ΔCt values are displayed with error bars indicating SEM. Gapdh mRNA was used as a control. PD is Parkinson's disease and C is control.
Figure 5:
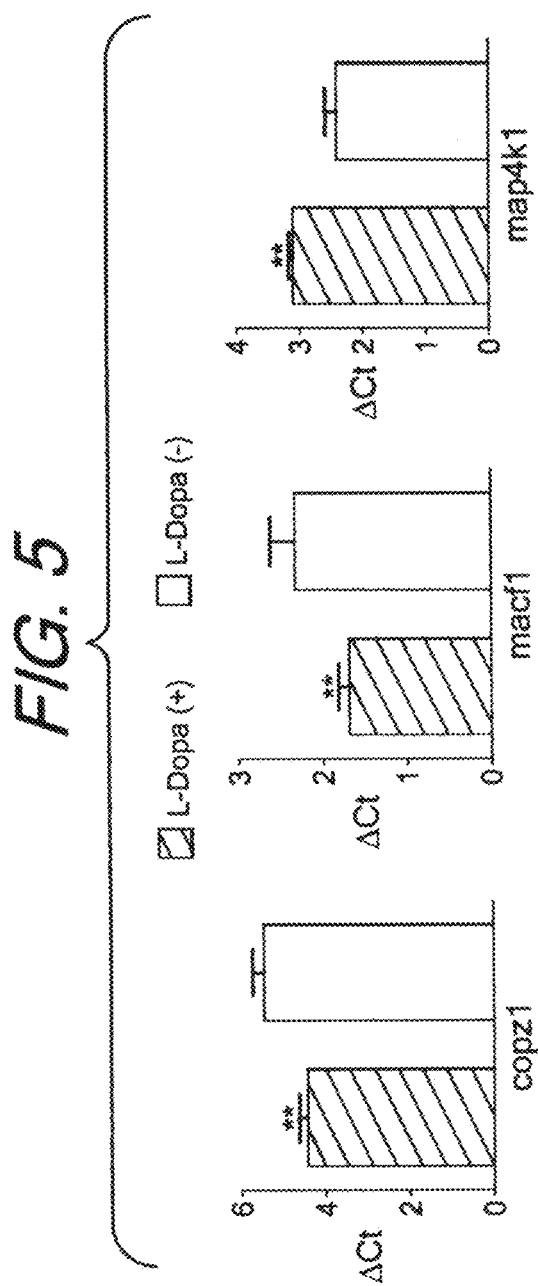
FIG. 5 is a Pearson correlation analysis between expression of copz1, macf1 and map4k1 and dopamine therapy. The solid bar represents study participants that received dopamine therapy and the open bar represents study participants who did not receive dopamine therapy. *p<0.01, p<0.001 and *p<0.0001

Heat map analysis indicated that PD patients can be clustered together using the 14 validated biomarkers (FIG. 2B). PCA analysis of the validated biomarkers indicated that PD patients can be distinguished from controls (FIG. 2C). In order to determine whether medication that the PD patients received affected expression of the biomarkers, Pearson correlation analysis was conducted and the results revealed that copz1, macf1 and map4k1 expression correlated with dopamine therapy (FIG. 5).

In order to assess the performance of the biomarkers in the classification of unknown samples, we carried out a prediction for PD or 'non-PD' phenotype (a two-class prediction) in a test set containing 53 participants including PD patients as well as healthy and disease controls (MSA and PSP). The results from the blinded samples are presented in FIG. 1B. If a study participant had at least 5 biomarkers that indicated that the individual was a PD patient, then the participant was labeled PD. One individual had an equal number of biomarkers that indicated that he/she was a PD patient or a PSP patient. The results indicated that we are able to identify PD patients with 90% accuracy (P=0.0001) and 94% sensitivity (P=0.00001) in accordance with the clinical diagnosis. These results suggest that using the fourteen splice variant-specific biomarkers shown in FIG. 6 one may identify samples as PD or non-PD.

LITERATURE CITED

1. Miller R M & Federoff H J (2005) Altered gene expression profiles reveal similarities and differences between Parkinson disease and model systems. *Neuroscientist* 11(6):539-549.
2. Moran L B, et al. (2006) Whole genome expression profiling of the medial and lateral substantia nigra in Parkinson's disease. *Neurogenetics* 7(1):1-11.

3. Moran L B & Graeber M B (2008) Towards a pathway definition of Parkinson's disease: a complex disorder with links to cancer, diabetes and inflammation. *Neurogenetics* 9(1):1-13.
4. Meredith E J, Chamba A, Holder M J, Barnes N M, & Gordon J (2005) Close encounters of the monoamine kind: immune cells betray their nervous disposition. *Immunology* 115(3):289-295.
5. Gordon J & Barnes N M (2003) Lymphocytes transport serotonin and dopamine: agony or ecstasy? *Trends Immunol* 24(8):438-443.
6. McKenna F, et al. (2002) Dopamine receptor expression on human T- and B-lymphocytes, monocytes, neutrophils, eosinophils and NK cells: a flow cytometric study. *J Neuroimmunol* 132(1-2):34-40.
7. Mill J, Asherson P, Browes C, D'Souza U, & Craig I (2002) Expression of the dopamine transporter gene is regulated by the 3' UTR VNTR: Evidence from brain and lymphocytes using quantitative RT-PCR. *Am J Med Genet* 114(8):975-979.
8. Caronti B, et al. (1999) Reduced dopamine in peripheral blood lymphocytes in Parkinson's disease. *Neuroreport* 10(14):2907-2910.
9. Barbanti P, et al. (1999) Increased expression of dopamine receptors on lymphocytes in Parkinson's disease. *Mov Disord* 14(5):764-771.
10. Kipnis J, et al. (2004) Dopamine, through the extracellular signal-regulated kinase pathway, downregulates CD4+ CD25+ regulatory T-cell activity: implications for neurodegeneration. *J Neurosci* 24(27):6133-6143.
11. Ilani T, Strous R D, & Fuchs S (2004) Dopaminergic regulation of immune cells via D3 dopamine receptor: a pathway mediated by activated T cells. *Faseb J* 18(13):1600-1602.
12. Brochard V, et al. (2009) Infiltration of CD4+ lymphocytes into the brain contributes to neurodegeneration in a mouse model of Parkinson disease. *J Clin Invest* 119(1):182-192.
13. Scherzer C R, et al. (2007) Molecular markers of early Parkinson's disease based on gene expression in blood. *Proc Natl Acad Sci USA* 104(3):955-960.
14. Scherzer C R, et al. (2008) GATA transcription factors directly regulate the Parkinson's disease-linked gene alpha-synuclein. *Proc Natl Acad Sci USA* 105(31):10907-10912.
15. Tan E K, et al. (2005) Differential expression of splice variant and wild-type parkin in sporadic Parkinson's disease. *Neurogenetics* 6(4):179-184.
16. Shehadeh L A, et al. (2011) SRRM2, a potential blood biomarker revealing high alternative splicing in Parkinson's disease. *PLoS One* 5(2):e9104.
17. Ravina B, et al. (2009) A longitudinal program for biomarker development in Parkinson's disease: a feasibility study. *Mov Disord* 24(14):2081-2090.
18. Hughes A J, Daniel S E, Kilford L, & Lees A J (1992) Accuracy of clinical diagnosis of idiopathic Parkinson's disease: a clinico-pathological study of 100 cases. *J Neurol Neurosurg Psychiatry* 55(3): 181-184.
19. Gilman S, et al. (2008) Second consensus statement on the diagnosis of multiple system atrophy. *Neurology* 71(9):670-676.
20. Litvan I, et al. (1996) Clinical research criteria for the diagnosis of progressive supranuclear palsy (Steele-Richardson-Olszewski syndrome): report of the NINDS-SPSP international workshop. *Neurology* 47(1):1-9.
21. Turner L, Heath J D, & Kurn N (Gene expression profiling of RNA extracted from FFPE tissues: NuGEN technologies' whole-transcriptome amplification system. *Methods Mol Biol* 724:269-280.

What is claimed is:

1. A kit for diagnosing the presence of Parkinson's disease in a human subject comprising:
   14 containers each containing a forward and reverse primer pair to amplify one of each of a splice variant having Sequence ID Nos. 1-14 and power SYBR® dye; and
   a set of instructions on the conditions for conducting real time PCR on a test sample and for diagnosing Parkinson's disease.

2. The kit of claim 1 wherein the test sample comprises RNA molecules extracted from a whole blood sample of the human subject.

* * * * *

SEQUENCE LISTING

```
<160> NUMBER OF SEQ ID NOS: 46

<210> SEQ ID NO 1
<211> LENGTH: 130
<212> TYPE: RNA
<213> ORGANISM: Homo sapiens

<400> SEQUENCE: 1
cacagccagc cgacuuccug gugacggagg uggaaaaugg uggcuccuug ggcagcaaga    60
agggugugaa ccuuccuggg gcugcugugg acuugccugc uguguggag aaggacaucc   120 aggaucugaa                                                          130

<210> SEQ ID NO 2
<211> LENGTH: 72
<212> TYPE: RNA
<213> ORGANISM: Homo sapiens

<400> SEQUENCE: 2
gacauggugg auccugugaa acugcgccag ucuauccgca caguucuuuu caaccagugc    60
augauaucuu uc                                                        72

<210> SEQ ID NO 3
<211> LENGTH: 60
<212> TYPE: RNA
<213> ORGANISM: Homo sapiens

<400> SEQUENCE: 3
```

```
augaggcgcu ccaggaagag acacgugugg cccagaagga acuggaggaa gcagugaccu    60
```

<210> SEQ ID NO 4
<211> LENGTH: 62
<212> TYPE: RNA
<213> ORGANISM: Homo sapiens

<400> SEQUENCE: 4

```
cgggagccug acaguuuuu gacggugcag ucuugcuaua ggugugaga aauggcugua    60 gg                                                                 62
```

<210> SEQ ID NO 5
<211> LENGTH: 90
<212> TYPE: RNA
<213> ORGANISM: Homo sapiens

<400> SEQUENCE: 5

```
ggaccuggug gcacugaaga uggugaagau ggagccugau gaugaugucu ccacccuuca    60
gaaggaaauc cucauauuga aaacuugccg                                     90
```

<210> SEQ ID NO 6
<211> LENGTH: 67
<212> TYPE: RNA
<213> ORGANISM: Homo sapiens

<400> SEQUENCE: 6

```
caagcuaaac aaccaaauca gagaaaaugc agaagucucc auggacguuu cccuggcuua    60
ccgugau                                                              67
```

<210> SEQ ID NO 7
<211> LENGTH: 58
<212> TYPE: RNA
<213> ORGANISM: Homo sapiens

<400> SEQUENCE: 7

```
cacucaugug ccugcaugcu gccauaggau cauugcuggg cauagcagcg gcccuguu     58
```

<210> SEQ ID NO 8
<211> LENGTH: 62
<212> TYPE: RNA
<213> ORGANISM: Homo sapiens

<400> SEQUENCE: 8

```
gcauagcagc gggacucagu cuuucagccc cauugagga caucuacuuu ggacucuggg    60
gu                                                                  62
```

<210> SEQ ID NO 9
<211> LENGTH: 115
<212> TYPE: RNA
<213> ORGANISM: Homo sapiens

<400> SEQUENCE: 9

```
agcaggcgag agauggauga ugaugacgac gacgaugacg uaggagauca ugacgaugac    60
cacccuggga uggagguggu gcugcaugag gacaagaagu acuacccaac agccg        115
```

<210> SEQ ID NO 10
<211> LENGTH: 70
<212> TYPE: RNA
<213> ORGANISM: Homo sapiens

```
<400> SEQUENCE: 10
gauuuugugg ugggaaagag uuggucccug gcaagguaua aauuauauca aagaucuagg    60
ggagcuguca                                                          70

<210> SEQ ID NO 11
<211> LENGTH: 63
<212> TYPE: RNA
<213> ORGANISM: Homo sapiens

<400> SEQUENCE: 11 ggguucgcuac ggacuuaaaa ucuccgcacc gcacccucca ccucagaaac guuccuggau   60
ccg                                                                 63

<210> SEQ ID NO 12
<211> LENGTH: 62
<212> TYPE: RNA
<213> ORGANISM: Homo sapiens

<400> SEQUENCE: 12
gaggcuguau cgcauccauu gaauacugug accgaggaca uguacaccaa cgggucuccu    60
gc                                                                  62

<210> SEQ ID NO 13
<211> LENGTH: 59
<212> TYPE: RNA
<213> ORGANISM: Homo sapiens

<400> SEQUENCE: 13
ggcccggcgc agauccucug ugguuguuga auuguaacaa gagagagaac ucuggcugc     59

<210> SEQ ID NO 14
<211> LENGTH: 94
<212> TYPE: RNA
<213> ORGANISM: Homo sapiens

<400> SEQUENCE: 14
ucaguugcca aucucaagca aagcaaacau aagccaguuu uaaucuacuu uuuaagaaaa    60
gugguagucc uuuucacagu gccugacgug uggc                               94

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacagccagc cgacttcct                                                19

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttcagatcct ggatgtcctt ctc                                           23
```

```
<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacatggtgg atcctgtgaa act                                               23

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaaagatatc atgcactggt tgaaa                                             25

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgaggcgct ccaggaaga                                                    19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggtcactgc ttcctccagt tc                                                22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgggagcctg gacagtttt                                                    19

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctacagcca tttctcacac cat                                               23

<210> SEQ ID NO 23
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggacctggtg gcactgaaga                                                   20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cggcaagttt tcaatatgag gat                                               23

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caagctaaac aaccaaatca gagaaa                                            26

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atcacggtaa gccagggaaa                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cactcatgtg cctgcatgct                                                   20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aacagggccg ctgctatg                                                     18

<210> SEQ ID NO 29
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcatagcagc gggactcagt                                              20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
accccagagt ccaaagtaga tgtc                                         24

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agcaggcgag agatggatga                                              20

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggctgttgg gtagtacttc ttg                                          23

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gattttgtgg tgggaaagag t                                            21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgacagctcc cctagatctt tg                                           22

<210> SEQ ID NO 35
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 35
gggtcgctac ggacttaaaa tct                                          23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cggatccagg aacgtttctg                                              20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaggctgtat cgcatccatt g                                            21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcaggagacc cgttggtgta                                              20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaggctgtat cgcatccatt g                                            21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcaggagacc cgttggtgta                                              20

<210> SEQ ID NO 41
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 41
ggcccggcgc agat                                                       14

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcagccagag ttctctctct tgt                                             23

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcagttgcca atctcaagca a                                               21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccacacgtc aggcactgt                                                  19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caacggattt ggtcgtattg g                                               21

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgatggcaac aatatccact ttacc                                           25
```